US012605149B2

(12) United States Patent     (10) Patent No.:   US 12,605,149 B2
Liu et al.                       (45) Date of Patent:      Apr. 21, 2026

(54) COLLECTION DEVICE WITH A VALVE FOR A LIQUID SPECIMEN

(71) Applicant: Zhongshan Ophthalmic Center of Sun Yat-Sen University, Guangzhou (CN)

(72) Inventors: Yizhi Liu, Guangzhou (CN); Yan Luo, Guangzhou (CN); Xiaofeng Lin, Guangzhou (CN); Lin Lu, Guangzhou (CN)

(73) Assignee: Zhongshan Ophthalmic Center of Sun Yat-Sen University, Guangzhou (CN)

( * ) Notice: Subject to any disclaimer, the term of this patent is extended or adjusted under 35 U.S.C. 154(b) by 861 days.

(21) Appl. No.: 16/980,417

(22) PCT Filed: May 30, 2018

(86) PCT No.: PCT/CN2018/089107
§ 371 (c)(1),
(2) Date: Sep. 13, 2020

(87) PCT Pub. No.: WO2019/196175
PCT Pub. Date: Oct. 17, 2019

(65) Prior Publication Data
US 2021/0000454 A1     Jan. 7, 2021

Related U.S. Application Data

(63) Continuation-in-part of application No. PCT/CN2018/082719, filed on Apr. 11, 2018.

(51) Int. Cl.
*A61B 10/00*        (2006.01)

(52) U.S. Cl.
CPC .... *A61B 10/0045* (2013.01); *A61B 2010/009* (2013.01)

(58) Field of Classification Search
CPC .......... A61B 10/0045; A61B 2010/009; A61B 10/0283; A61M 39/22; A61M 1/00; A61F 9/00736
See application file for complete search history.

(56) References Cited

U.S. PATENT DOCUMENTS 4,972,843 A * 11/1990 Broden ............ A61B 5/150534
                                       600/576
2004/0068291 A1* 4/2004 Suzuki ................... A61B 10/06
                                       606/205

(Continued)

FOREIGN PATENT DOCUMENTS

CN     204637081 U     9/2015
CN     205235026 U     5/2016
(Continued)

OTHER PUBLICATIONS

International Search Report issued by China National Intellectual Property Administration (CNIPA) published on Jan. 7, 2019 regarding PCT/CN18/89107, Beijing, China.

*Primary Examiner* — Tse W Chen
*Assistant Examiner* — Joseph A Tombers
(74) *Attorney, Agent, or Firm* — AVEK IP, LLC

(57) ABSTRACT

Collection devices with valves for liquid specimens are disclosed. In an embodiment, the disclosure provides a collection device including a reservoir having a sealed cavity, the sealed cavity being under a negative pressure; a delivery tube in communication with the sealed cavity of the reservoir and having a delivery inlet, a delivery outlet, and a valve disposed between the delivery inlet and the delivery outlet, the valve being configured to control the communication and blocking between the delivery inlet and the delivery outlet, and an angle being formed by an extension line of the delivery inlet an extension line of the delivery (Continued)

outlet; and a piercing component for piercing a tissue is connected with the delivery inlet of the delivery tube.

19 Claims, 6 Drawing Sheets

(56)                    References Cited

U.S. PATENT DOCUMENTS

| 2009/0318856 A1 * | 12/2009 | Glaser ................ | A61B 10/0045 |
| | | | 604/35 |
| 2014/0155782 A1 * | 6/2014 | Bullington ....... | A61B 5/150221 |
| | | | 600/575 |
| 2017/0027551 A1 * | 2/2017 | O'Callaghan ......... | A61M 39/22 |

FOREIGN PATENT DOCUMENTS

| CN | 106730169 | A | 5/2017 |
| CN | 206612801 | U | 11/2017 |
| CN | 108433748 | A | 8/2018 |
| JP | 2008206734 | A | 9/2008 |

* cited by examiner

COLLECTION DEVICE WITH A VALVE FOR A LIQUID SPECIMEN

CROSS REFERENCE TO RELATED APPLICATIONS

This application is the United States national stage entry under 35 U.S.C. 371 of PCT/CN2018/089107 filed on May 30, 2018, which claims priority to Chinese priority number PCT/CN2018/082719 filed on Apr. 11, 2018, the disclosure of which are incorporated by reference herein in their entireties.

FIELD OF THE DISCLOSURE

The disclosure relates generally to medical instruments. More specifically, the disclosure relates to collection devices with valves for a liquid specimens.

BACKGROUND

In medical research, liquid specimens obtained from tissues are generally used in clinical practice and scientific research. For example, for clinical specimen commonly used in ophthalmology, liquid specimens such as aqueous humor and vitreous humor are very valuable for etiological diagnosis and treatment guidance of various retinal diseases and uveitis, as well as lowering intraocular pressure (TOP) for glaucoma. Therefore, effective collection and preservation of liquid specimens is also an important part of clinical surgeries and other treatment processes For liquid specimens, for example, in ophthalmology, paracentesis was once the main method for obtaining liquid specimens, but this method has high demand on doctors' surgical skills and collection positions. In addition, the operation process of paracentesis is poorly controllable, since doctors need to extract liquid specimens from tissues manually. Currently, the commonly used method for liquid specimen collection in ophthalmology has the following problems: (1) Intraocular liquid available to be collected for a specimen is spare. For example, assuming that when a paracentesis is ongoing on an anterior chamber to collect the humor, complications may be caused easily since the eyeball must be pressed for multiple times to obtain a sufficient amount of specimen. (2) The syringe is used as a collection device for a liquid specimen, but this method requires the surgeon to operate with both hands at the same time, which is poorly controllable. Therefore, it may be prone to cause an excessive extraction and therefore may cause surgical complications. (3) A great loss might be caused, since the specimen, hard to be obtained, is stored in the needle portion. (4) There are multiple procedures to transfer a specimen collected on an operating table to a reservoir for storage, increasing the workload of the doctor to take the specimen. (5) There is no good minimally invasive method for collecting vitreous humor. Effective minimally invasive methods for collecting vitreous humor are not yet developed except vitrectomy in which surgeon obtains vitreous humor in large amount.

SUMMARY

The following presents a simplified summary of the invention to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, the disclosure provides a collection device with a valve for a liquid specimen, including a reservoir having a sealed cavity, the sealed cavity being under negative pressure; a delivery tube in communication with the sealed cavity of the reservoir and having a delivery inlet, a delivery outlet, and a valve disposed between the delivery inlet and the delivery outlet, the valve being configured to control the communication and blocking between the delivery inlet and the delivery outlet, and an angle is formed by an extension line of the delivery inlet and an extension line of the delivery outlet; and a piercing component for piercing a tissue and in communication with the delivery inlet of the delivery tube.

Optionally, in the collection device according to the disclosure, the reservoir is detachably connected to the delivery tube. In this way, after the liquid specimen has been collected into the reservoir, the reservoir may be conveniently separated to perform subsequent test steps directly.

Optionally, in the collection device according to the disclosure, the valve may be a press-type mechanical valve. In this way, it may be convenient for an operator such as a doctor to operate the valve of the delivery tube to control the collection of the liquid specimen conveniently.

Optionally, in the collection device according to the disclosure, in the collection device, the liquid specimen may be aqueous humor in the eye. In such case, aqueous humor in the eye may be collected in an automatic and convenient way by taking the advantage of the negative pressure (for example, lower than intraocular pressure) within the reservoir.

Optionally, in the collection device according to the disclosure, the piercing component may be provided with a limit mechanism for limiting a piercing position. By doing this, the piercing position pierced by the piercing component may be controlled in a more accurate way, which may help to improve the reliability of the surgery.

Optionally, in the collection device according to the disclosure, the angle formed by the extension line of the delivery inlet and the extension line of the delivery outlet may be 30-120 degrees or 180-300 degrees. In such case, a doctor or the like may conveniently operate the piercing component, and adverse effects by the reservoir and the delivery tube on the operation of the piercing component may be avoided.

Optionally, in the collection device according to the disclosure, the reservoir may be a transparent tube. In this way, it may be convenient for the operator such as a doctor to observe the state of collection of the liquid specimen in the reservoir in real time.

Optionally, in the collection device according to the disclosure, the reservoir may be provided with scales. In this way, the operator such as a doctor may get to know the amount of the liquid specimen that has been collected in real time.

Optionally, in the collection device according to the disclosure, the collection device includes a sleeve cap which detachably covers the piercing component. In this way, it may be ensured that the collection device is in a sealed state, and an operator may be prevented from being injured by the piercing component.

Optionally, in the collection device according to the disclosure, the piercing component may be a syringe. In this way, it may be convenient for the operator such as a doctor to pierce a tissue to collect a liquid specimen.

Optionally, in the collection device according to the disclosure, the reservoir may be provided with non-slip ribs on an outer surface. In this way, it may be convenient for the operator such as a doctor to remove the reservoir.

BRIEF DESCRIPTION OF THE DRAWINGS

Illustrative embodiments of the present disclosure are described in detail below with reference to the figures.

DETAILED DESCRIPTION

Figure 1:
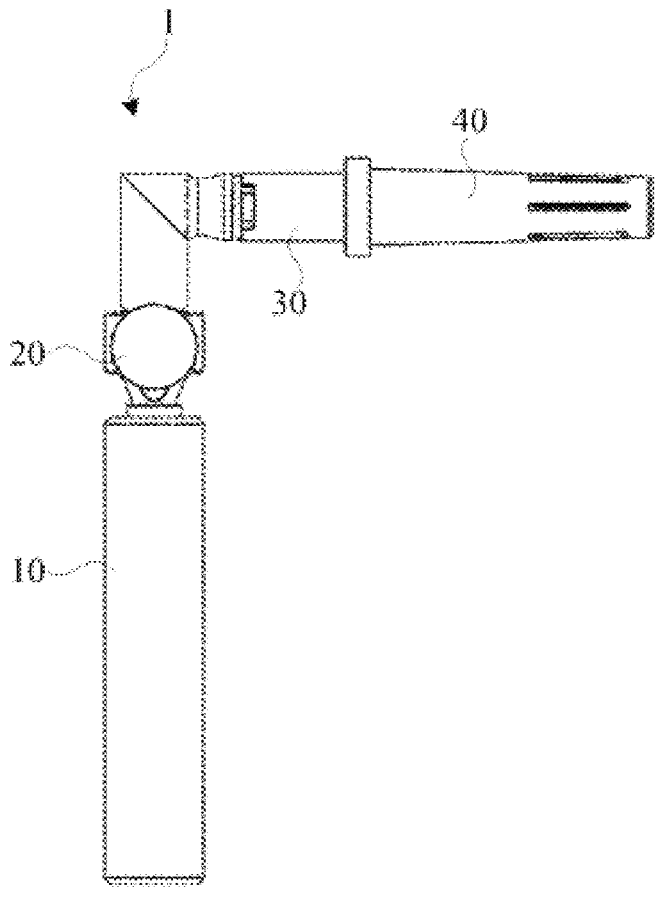
FIG. 1 is a schematic diagram of the collection device with a valve for a liquid specimen according to an embodiment of the disclosure.

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

Hereinafter, preferred embodiments of the disclosure will be described in detail with reference to the accompanying drawings. In the following description, the same reference numerals are given to the same components, and repeated descriptions are omitted. In addition, the accompanying drawings are for illustrative purposes only, and the ratio of the dimensions of the components to each other or the shapes of the components may be different from the actual.

It should be noted that the terms "comprises" and "has", as well as any variations thereof, for example a process, method, system, product or apparatus that comprises or has a series of steps or elements are not necessarily limited to those steps or elements expressly listed, but may comprise or have other steps or elements that are not expressly listed or inherent to the process, method, system, product, or apparatus.

4

Figure 2:
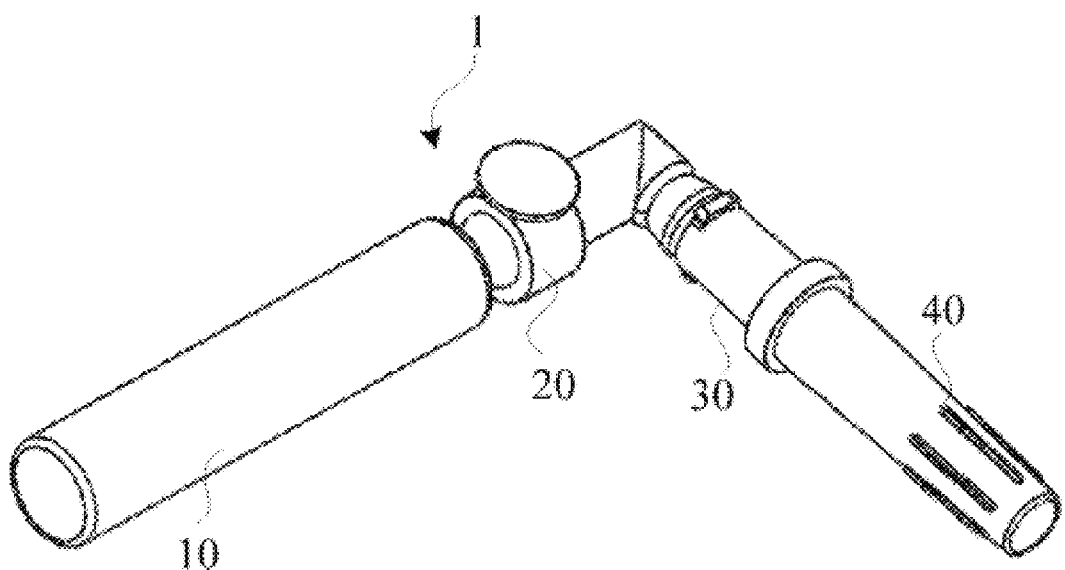
FIG. 2 is a three-dimensional structural diagram of the collection device with a valve for the liquid specimen according to an embodiment of the disclosure.
Figure 3:
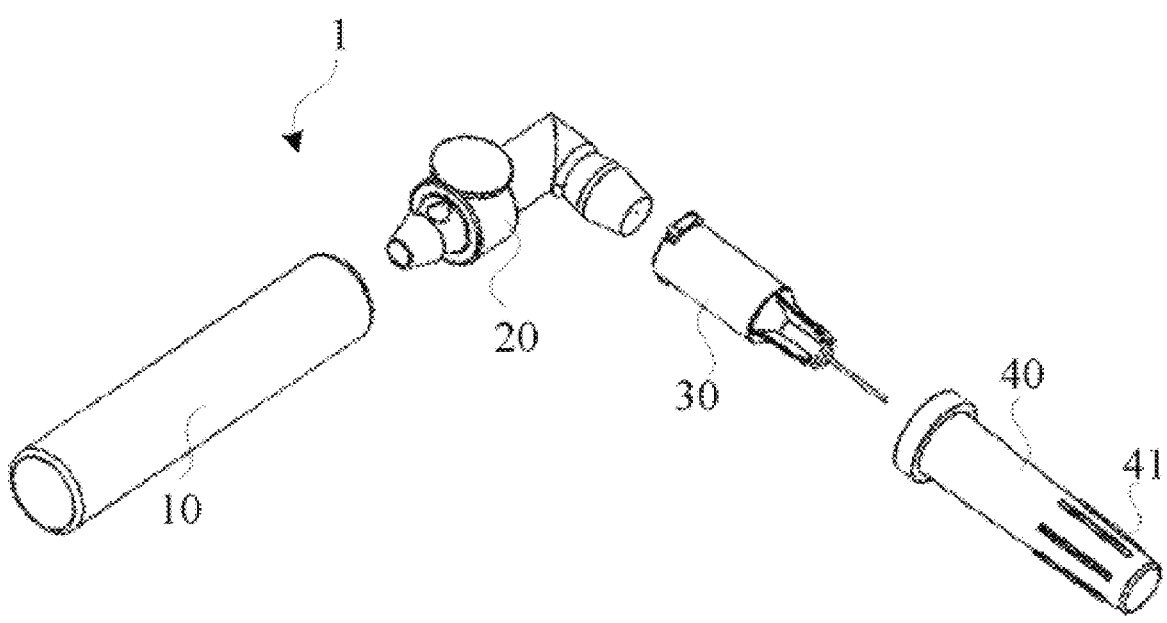
FIG. 3 is a decomposition diagram of the collection device shown in FIG. 2 according to an embodiment of the disclosure.

FIG. 1 is a schematic diagram of the collection device with a valve according to an embodiment of the disclosure; FIG. 2 is a three-dimensional structural diagram of the collection device with a valve for the liquid specimen according to an embodiment of the disclosure; and FIG. 3 is a decomposition schematic diagram of the collection device shown in FIG. 2.

As shown in FIG. 1, the collection device with a valve for the liquid specimen (hereinafter sometimes referred to as "collection device") 1 includes a reservoir 10, a delivery tube 20, and a piercing component 30. The delivery tube 20 has valve 23 (described later) configured to control communication between the reservoir 10 and the piercing component 30. Therefore, an operator such as a doctor, a nurse, or other professional person may conveniently collect a liquid specimen via an automatic process under negative pressure by piercing a tissue (such as the anterior chamber of the eye) with the piercing component 30, and may conveniently perform subsequent tests directly on the collected liquid specimen stored in the reservoir.

In this embodiment, the reservoir 10 may have a sealed cavity 11. The sealed cavity 11 is under negative pressure. Here, the negative pressure is set according to different uses, that is, the sealed cavity 11 of the reservoir 10 may be made to be under different negative pressures according to liquid specimens to be collected from different tissues, and then the negative pressure is defined as the air pressure in the sealed cavity 11 being lower than the air pressure in the tissues. For example, for a liquid specimen in the eye, such as aqueous humor, the corresponding negative pressure is lower than the intraocular pressure.

In some examples, the sealed cavity 11 may form a negative pressure environment with an air pressure lower than a specified air pressure, which may help to implement an automatic collection of a liquid specimen. In addition, to better utilize negative pressure for automatic collection, the pressure in the sealed cavity 11 is generally lower than the pressure within a tissue. In some examples, the air pressure in the sealed cavity 11 may be set to, for example, 5000 Pa, 1000 Pa, 500 Pa, 100 Pa, etc., depending on different uses.

In addition, the capacity of the sealed cavity 11 of the reservoir 10 is not particularly limited, and may be 1 mL to 20 mL, 20 mL to 50 mL, or 1 mL to 100 mL. For example, for a liquid specimen in ophthalmology, the volume (capacity) of the sealed cavity 11 might be 0.05 mL to 0.1 mL, 0.1 mL to 0.20 mL, or 0.20 mL to 0.50 mL.

In some examples, the collection device 1 according to this embodiment may be configured into different models, and accordingly, the capacity and the magnitude of negative pressure in the reservoir 10 may be different. Therefore, the applicability of the collection device 1 may be improved.

In some examples, the reservoir 10 may be a hollow cylinder. In other examples, the reservoir 10 may be a hollow cuboid, a hollow polygonal prism, or the like. Therefore, the collection device may be adapted to collection of liquid specimens for different purposes.

In some examples, the bottom of the reservoir 10 may be flat, which may facilitate placement of the reservoir 10. In addition, in some examples, the bottom of the reservoir 10 may be concave. In such case, the placement of the reservoir 10 is also facilitated.

In some examples, the reservoir 10 may be made of a material such as plastic, glass, or metal. In this way, in practical clinical applications, an operator such as a doctor may select reservoirs 10 made of different materials for different liquid specimens.

In some examples, the reservoir 10 may be a transparent tube so that it may be convenient for the operator to observe the state of collection of the liquid specimen in the reservoir in real time. In some examples, the reservoir 10 may be a transparent glass or plastic tube. Furthermore, in some examples, the reservoir 10 may be provided with scales. For example, the reservoir 10 may be provided with scales indicating the volume of the reservoir on an outer surface of the reservoir 10. In such case, an operator such as a doctor may get to know the amount of the liquid specimen that has been collected in real time.

In some examples, the scales on the reservoir 10 may be provided along with the outer surface of the reservoir 10, and the readings of the graduated markings increase in order from the bottom of the reservoir 10, for example, 0 μL, 5 μL, 10 μL, . . . , 100 μL, 200 μL, et cetera. However, the disclosure is not limited thereto, for example, the readings of the graduated markings may increase in order from a joint between the reservoir 10 and the delivery tube 20 to the bottom of the reservoir 10, for example, 0 μL, 5 μL, 10 μL, . . . , 100 μL, 200 μL, et cetera.

In some examples, the liquid specimen collected by the collection device 1 may be the aqueous humor in the eye. In such case, aqueous humor in the eye may be collected conveniently via an automatic process through a negative pressure (lower than intraocular pressure) within the reservoir 10.

In some examples, when the collection device 1 is used to collect aqueous humor in the eye, the collection amount of aqueous humor is small, for example, only 20-100 μL, and then, to effectively read the sealed cavity 11 of the reservoir 10, the reservoir 10 may be provided in a long and narrow shape. Optionally, the sealed cavity 11 of the reservoir 10 may be configured to have a lumen with a small bottom area and a large height.

In some examples, the reservoir 10 may be provided with a non-slip mechanism on the outer surface so that it may be convenient for an operator such as a doctor to remove the reservoir 10. In other examples, the reservoir 10 may be provided with multiple projections on the outer surface so that it may be convenient for the operator to remove the reservoir 10, and the reservoir 10 may be prevented from slipping and falling off from the operator's hand.

In some examples, the reservoir 10 may be further provided with a sealing cover (not shown). For example, when a liquid specimen has been collected into the reservoir 10, the reservoir 10 may be removed from the delivery tube 20 and covered by the sealing cover, which may help to ensure that the liquid specimen in the reservoir 10 is not polluted by the outside during subsequent operations, and subsequent storage or tests of the liquid specimen in the reservoir 10 may be facilitated.

Figure 4:
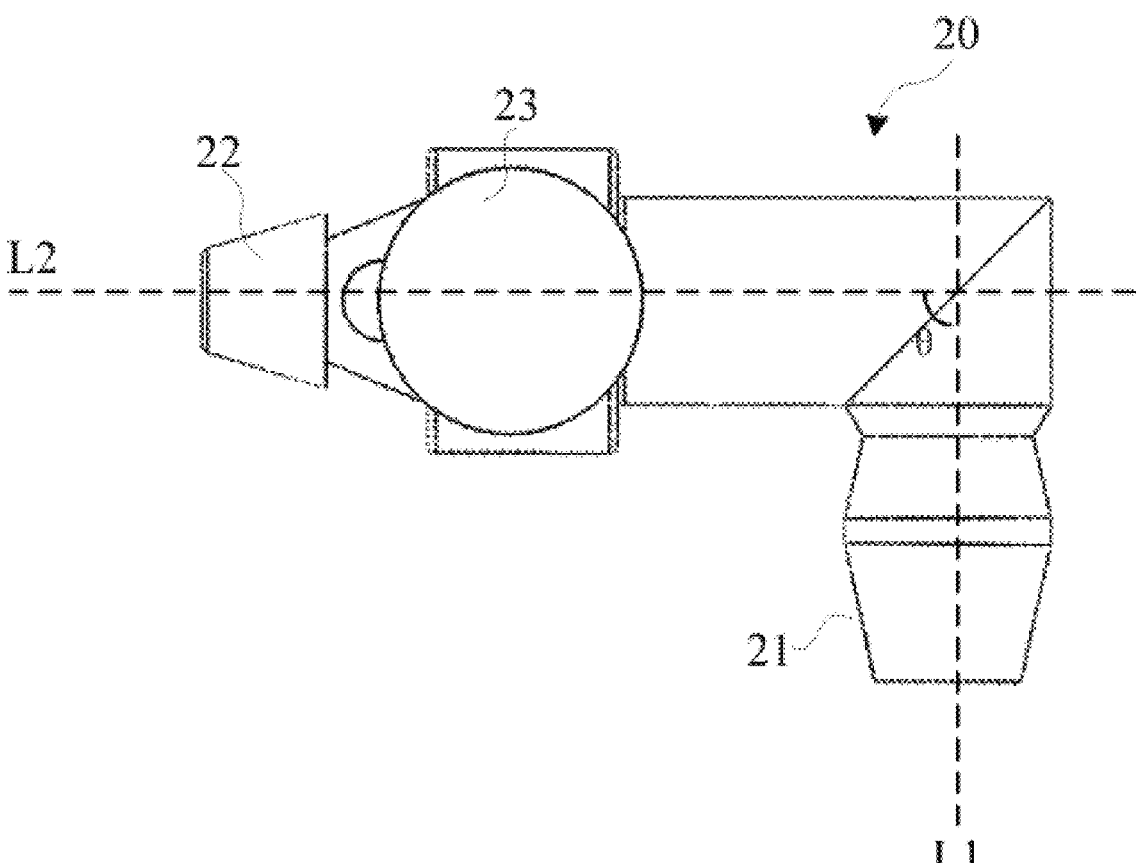
FIG. 4 is a schematic diagram of the delivery tube of the collection device shown in FIG. 2 according to an embodiment of the disclosure.
Figure 5:
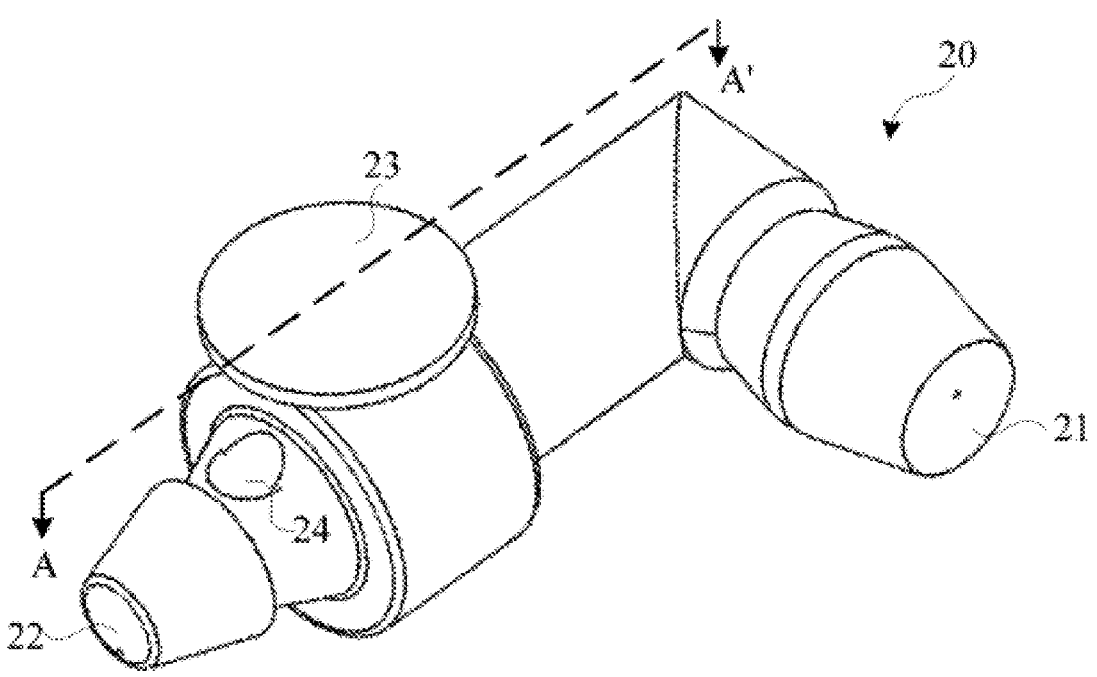
FIG. 5 is a three-dimensional structural diagram of the delivery tube of the collection device shown in FIG. 2 according to an embodiment of the disclosure.

FIG. 4 is a schematic diagram of a delivery tube of the collection device shown in FIG. 2; FIG. 5 is a three-dimensional structural diagram of the delivery tube of the collection device shown in FIG. 2; and FIG. 6 is a schematic cross-sectional diagram of the delivery tube along a line A-A' in FIG. 5.

Figure 6:
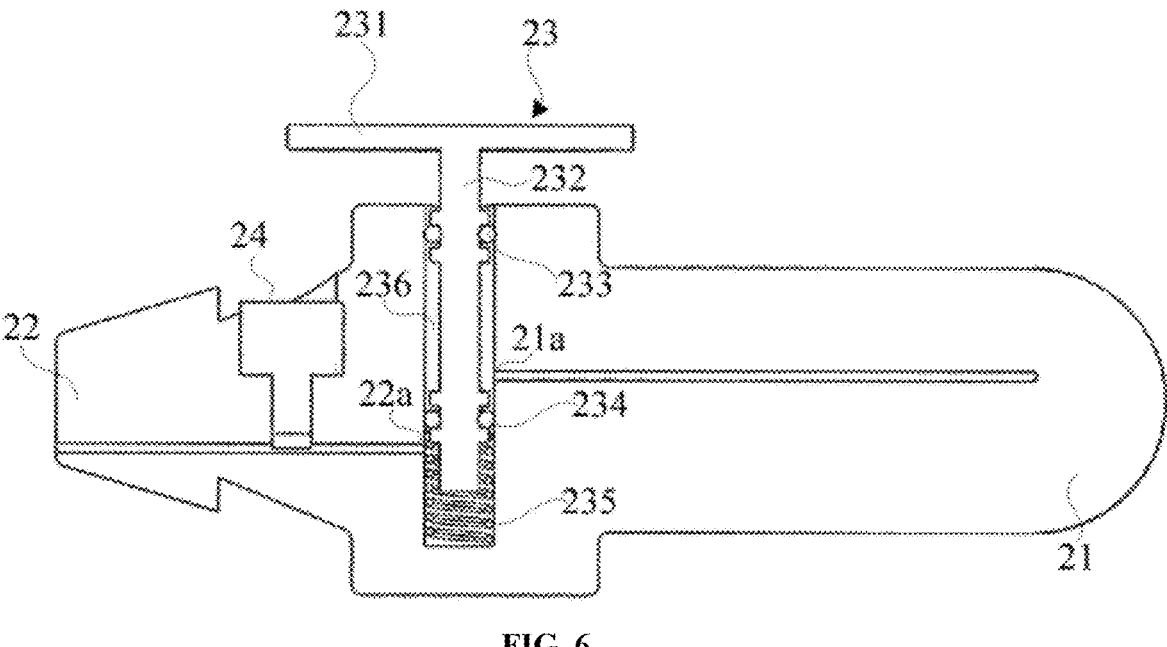
FIG. 6 is a schematic cross-sectional diagram of the delivery tube along a section line A-A' in FIG. 5 according to an embodiment of the disclosure.

As shown in FIGS. 4-6, in the collection device 1, the delivery tube 20 is connected to and in communication with the reservoir 10. That is, a channel is formed between the delivery tube 20 and the reservoir 10 (see FIG. 6 described later). Specifically, the delivery tube 20 may be in communication with the sealed cavity 11 of the reservoir 10, and as the sealed cavity 11 is under negative pressure, the liquid specimen may flow into the sealed cavity 11 of the reservoir 10 through the delivery tube 20.

In some examples, the delivery tube 20 may form a Luer connection with the reservoir 10. For example, one end of the delivery tube 20 is a Luer fitting which forms a Luer connection with the reservoir 10. In such case, the delivery tube 20 may be removably mounted to the reservoir 10.

In addition, the delivery tube 20 has a delivery inlet 21, a delivery outlet 22, and a valve 23 disposed between the delivery inlet 21 and the delivery outlet 22.

In this embodiment, the delivery inlet 21 may be connected to a piercing component 30 (described later), the delivery outlet 22 may be in communication with the reservoir 10, and the communication and blocking between the delivery inlet 21 and the delivery outlet 22 are controlled by the valve 23. In such case, the communication and blocking between the reservoir 10 and the piercing component 30, especially the liquid specimen in the tissue pierced by the piercing component 30, may be conveniently controlled by controlling the valve 23.

As described above, in the delivery tube 20, the valve 23 may control the communication and blocking between the delivery inlet 21 and the delivery outlet 22. In addition, an angle θ is formed by an extension line L1 of the delivery inlet 21 forms and an extension line L2 of the delivery outlet 22 (see FIG. 4). In some examples, the angle θ formed by the extension line of the delivery inlet 21 and the extension line of the delivery outlet 22 may be 30-330 degrees. In such case, a doctor or others may operate the piercing component 30 conveniently, and adverse effects caused by the reservoir 10 and the delivery tube 20 on the operation of the piercing component 30 is avoided.

Furthermore, in other examples, the angle θ formed by the extension line of the delivery inlet 21 and the extension line of the delivery outlet 22 may be 30-120 degrees or 180-300 degrees. In other examples, the angle θ formed by the extension line of the delivery inlet 21 and the extension line of the delivery outlet 22 may be 90 degrees or 270 degrees (see FIG. 4) so that it may be easier for the operator such as a doctor to operate the collection device 1.

In some examples, the reservoir 10 is detachably connected to the delivery tube 20. Therefore, after the liquid specimen has been collected into the reservoir 10, the reservoir 10 may be conveniently separated to perform subsequent test steps directly. For example, the reservoir 10 may be removed from the delivery tube 20, and subsequent medical tests may then be performed directly on the reservoir 10 with the liquid specimen, which may save test time and improve the clinical and medical efficiency. In some examples, the valve 23 may be a press-type mechanical valve. In such case, it may be convenient for an operator such as a doctor to use the valve 23 of the delivery tube to control the collection of the liquid specimen conveniently. Specifically, an operator such as a doctor may easily control the automatic collection of the liquid specimen by pressing the valve 23, which may improve the clinical surgery efficiency of the doctor or others.

As shown in FIG. 5 and FIG. 6, in this embodiment, the valve 23 may generally include a pressing unit 231, a rod body 232 connected to the pressing unit 231, an inner cavity cooperating with the rod body 232, seal ring 233 and seal ring 234 separately arranged at different positions on the rod body 232, and an elastic component 235 provided in the inner cavity 236.

In some examples, the pressing unit 231 may be circular pie-shaped so that it may be convenient for an operator such as a doctor to access and operate such as to press. In addition, as shown in FIG. 2, a case where the pressing unit 231 is disposed on one side of the valve 23 is shown, but the present disclosure is not limited thereto, in some examples, the pressing unit 231 may also be disposed on the other side of the valve 23.

In the valve 23, the elastic component 235 may be changed by pressing the pressing unit 231 so that the rod body 232 is provided with at least a first position and a second position in the inner cavity 236. For example, when the rod body 232 presses the spring 235 to be at the first position, one end 21a of the delivery inlet 21 and one end 22a of the delivery outlet 22 are between the sealing ring 233 and the sealing ring 234. Here, the delivery inlet 21 is in communication with the delivery outlet 22 via a space 236, and the reservoir 10 is in communication with the outside (tissue) via the delivery inlet 21, the delivery outlet 22 and the piercing component 30. For example, when the rod body 232 presses the spring 235 to be at the second position, for example, one end 21a of the delivery inlet 21 is between the sealing ring 233 and the sealing ring 234. Here, the delivery inlet 21 is not in communication with the delivery outlet 22, and the reservoir 10 is isolated from the outside. In this way, the opening and closing of the valve 23 may be controlled by pressing the pressing unit 231, which may help to conveniently implement and control communication and isolation between the reservoir 10 having a negative pressure environment and the outside.

In such embodiment, the material for making the valve 23 is not particularly limited. In some examples, the valve 23 may be made of materials such as plastic, glass, metal, et cetera. From the perspective of durability, the valve 23 may be made of a metal material.

Furthermore, the delivery tube 20 may be provided with an airtight plug 24 for evacuation to form negative pressure in the reservoir 10. Specifically, in a case where the delivery tube 20 (specifically, the delivery outlet 22 of the delivery tube 20) is in communication with the reservoir 10, for example, by inserting a syringe into a channel from the airtight plug 24 to the delivery outlet 22, and evacuating while keeping the valve 23 closed (at this time the delivery inlet 21 is not in communication with the delivery outlet 22.) In this way, a specified negative pressure (for example, lower than intraocular pressure) environment may be formed in the sealed cavity 11 of the reservoir 10 conveniently.

In addition, the airtight plug 24 may also maintain the negative pressure in the reservoir 10. Specifically, after evacuation via the airtight plug 24, the channel may be blocked as the airtight plug 24 may recover its original state. Therefore, the airtight plug 24 may still maintain the negative pressure environment of the reservoir 10. In some examples, the airtight plug 24 may be a rubber plug.

Furthermore, the reservoir 10 is connected to the delivery tube 20, and the airtight plug 24 is formed at one end close to the delivery outlet 22 of the delivery tube 20. To ensure that the airtight plug 24 may be used to provide an inlet for the negative pressure processing of the reservoir 10, at least one part of the airtight plug 24 needs to protrude from the reservoir 10 when the reservoir 10 is connected to the delivery tube 20, to allow, for example, a syringe for evacuation to be inserted into the airtight plug 24.

In some examples, the seal ring 233 and the seal ring 234 may be made of medical rubber such as silicone. In other examples, the seal ring 233 and the seal ring 234 may be alternatively made of other medical materials such as plastics, glass resins, artificial compounds, et cetera. Therefore, the air tightness of the valve 23 may be ensured while the requirements on material of medical instruments are satisfied.

In addition, in some examples, the valve 23 may be an electric valve. For example, the valve may be designated to detect both the change of the air pressure or the hydraulic pressure, the application of the electric valve allows it to automatically shut down as long as the electric valve detects the excessively low value of either the air pressure or hydraulic pressure so that the delivery inlet 21 is no longer in communication with the delivery outlet 22. In such case, it may be more convenient for an operator to control the valve 23.

Figure 7:
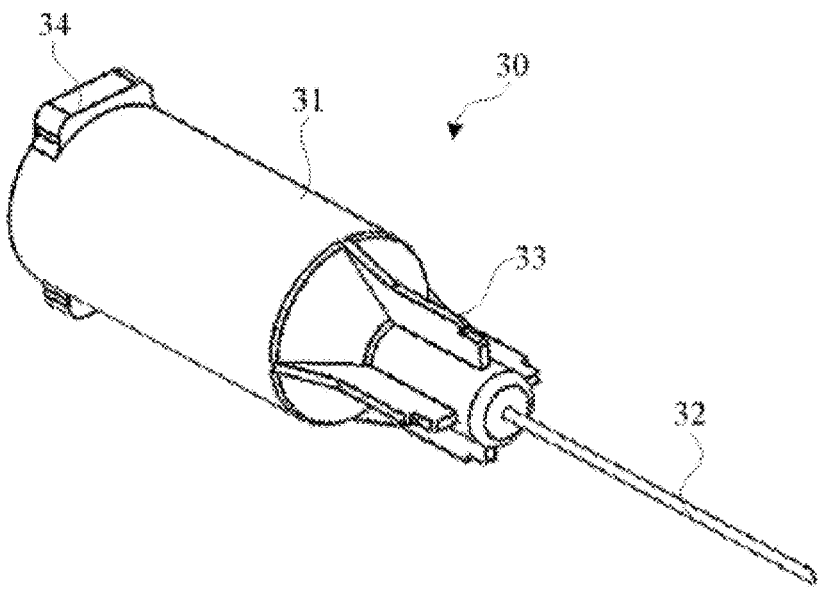
FIG. 7 is a three-dimensional structural diagram of a piercing component of the collection device according to an embodiment of the disclosure.
Figure 8:
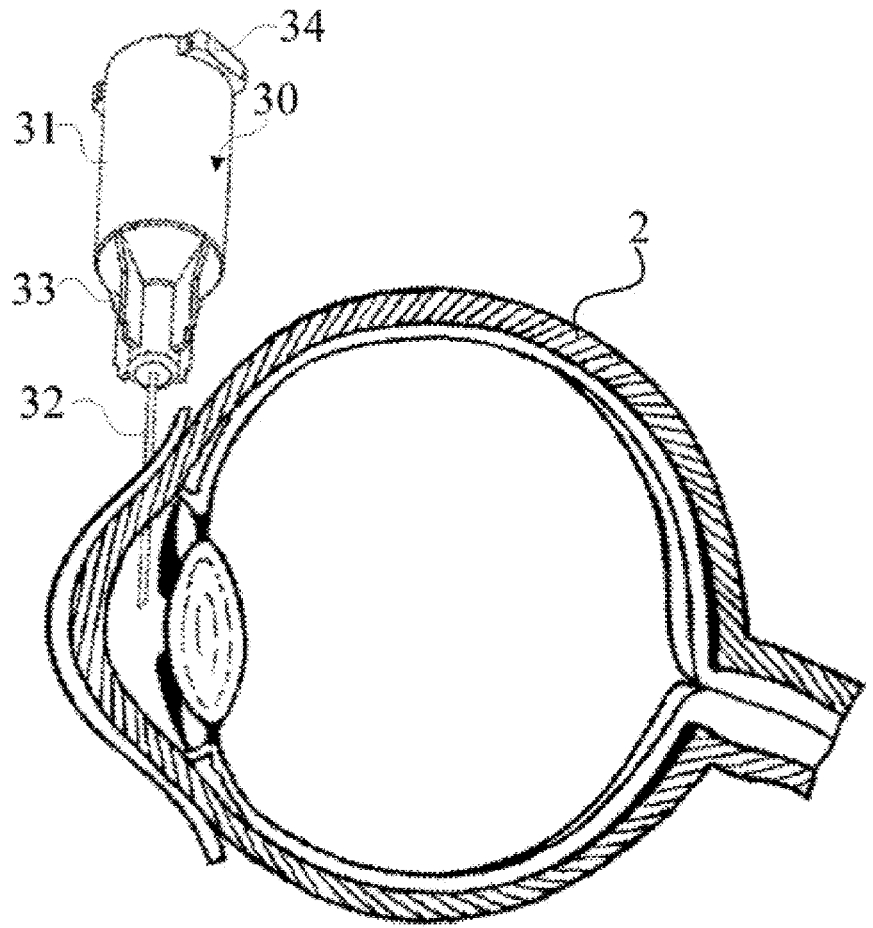
FIG. 8 is a schematic diagram showing a usage state of the piercing component of the collection device according to an embodiment of the disclosure.
Figure 9:
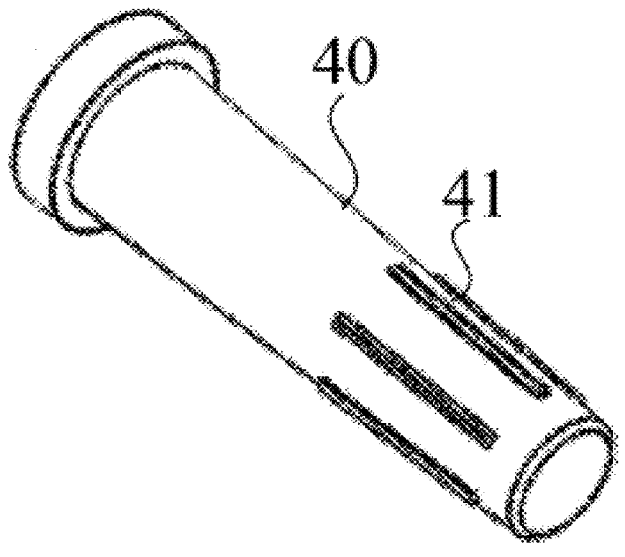
FIG. 9 is a three-dimensional structural diagram of a sleeve cap of the collection device according to an embodiment of the disclosure.
Figure 10:
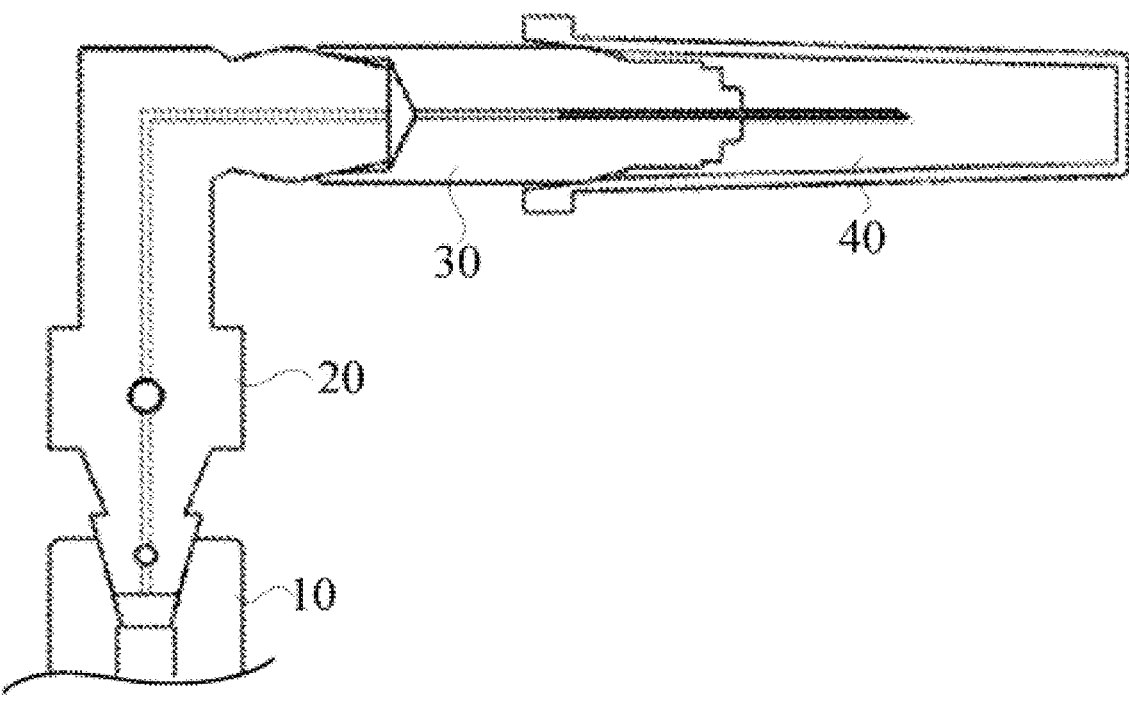
FIG. 10 is a schematic diagram of the channel of the collection device according to an embodiment of the disclosure.

FIG. 7 is a three-dimensional structural diagram of a piercing component of the collection device according to an embodiment of the disclosure. FIG. 8 is a diagram showing a usage state of the piercing component of the collection device in use according to an embodiment of the disclosure. FIG. 9 is a three-dimensional structural diagram of a sleeve cap of the collection device according to an embodiment of the disclosure. FIG. 10 is a schematic diagram of the channel this collection device use according to an embodiment of the disclosure. In FIG. 8, for the convenience of illustration of application examples, an example in which the collection device 1 is used to collect aqueous humor in an eyeball 2 is shown, but the disclosure is not limited thereto.

As shown in FIG. 7, the piercing component 30 may include a main body 31 and a piercing portion 32 connected to the main body 31. In addition, the main body 31 may be in communication with the piercing portion 32 so that a liquid specimen may flow to the delivery tube 20 through the piercing component 30.

In some examples, in the piercing component 30, a narrow channel is formed between the main body 31 and the piercing portion 32 (see FIG. 10), which may help to ensure that no loss of the liquid specimen will be caused because the liquid specimen will be retained in the main body 31 or in the piercing portion 32 when flowing through the piercing component 30. This structure is particularly suitable for use in cases where a small amount of liquid specimen, such as aqueous humor, is extracted.

In some examples, the piercing component 30 may form a Luer connection with the delivery tube 20. For example, one end, close to the delivery inlet 21, of the delivery tube 20 forms a Luer fitting to form a Luer connection with the piercing component 30.

In addition, in some examples, the piercing component 30 may be integrally formed with the delivery tube 20. In such case, the piercing component 30 may be a portion extending from the delivery tube 20.

In some examples, the piercing component 30 may be provided with a limit mechanism 33 for limiting a piercing position. Specifically, the limit mechanism 33 is provided between the main body 31 and the piercing portion 32 of the piercing component 30 to limit the piercing position. In such case, when a doctor or the like penetrates a tissue with the piercing component 30, the piercing (penetration) position of the piercing component 30 is limited so that the doctor or the like may control the depth of penetration of the piercing component 30 when they collect aqueous humor. Because of that, the piercing position of the piercing component 30 may be more accurately controlled, which may effectively prevent the patient from receiving a secondary injury due to excessive penetration and improving the reliability of the surgery.

In the description herein, the piercing position refers to a position where the piercing component 30 penetrates a tissue. Specifically, by penetrating into the tissue containing the liquid specimen, the liquid specimen in the tissue is enabled to communicate with the sealed cavity 11 of the reservoir 10, and then the liquid specimen in the tissue is automatically collected under the negative pressure in the reservoir 10.

In the example of the piercing component 30 penetrating into the eyeball 2 to obtain an aqueous humor specimen as shown in FIG. 8, the piercing position should avoid the iris and the cornea, to prevent damages on these tissues. In addition, it should be noted that the operating direction of the piercing component 30 as shown in FIG. 8 is only exemplary. Alternately, the piercing component 30 may also penetrate the anterior chamber of the eyeball in a direction substantially parallel to the iris to obtain an aqueous humor specimen.

In some examples, the limit mechanism 33 may be designed to conform to the surface of the tissue, which may help to automatically align the piercing portion 32 of the piercing component 30 to the piercing position. Therefore, it may be convenient for an operator such as a doctor to perform the piercing operation.

In some examples, the piercing component 30 may have a protrusion 34. With the protrusion 34, the piercing component 30 may be removed from or mounted to the delivery tube 20 easily. A pair of opposite protrusion 34 may be provided so that the piercing component 30 may be removed from or mounted to the delivery tube 20 more easily.

In some examples, the piercing component 30 may also be tapered along its length. Therefore, it may be convenient for the operator such as a doctor to pierce a tissue conveniently, which may improve the reliability and stability.

In addition, in some examples, the piercing component 30 may be a syringe. In such case, as the front end of the syringe is sharp, a tissue such as an eyeball may be easily pierced. Therefore, it may be convenient for an operator such as a doctor to pierce a tissue to collect a liquid specimen.

In some examples, a needle of the syringe works as the piercing component 30 may have an outer diameter of 0.31 mm to 4.57 mm and an inner diameter of 0.15 mm to 3.81 mm. For the collection of liquid specimens in ophthalmology, the needle of the syringe has an outer diameter of 0.31 mm to 0.64 mm and an inner diameter of 0.15 mm to 0.33 mm so that liquid specimens may be effectively collected with a minimized wound, which may help to implement safe and minimally invasive collection of specimens.

As described above, the reservoir 1, the delivery tube 2 and the piercing component 3 are connected and a narrow channel is formed therein (as shown in FIG. 10) so that the liquid specimen may be automatically collected into the reservoir 1 via the piercing component 3 and the delivery tube 2. In such case, the liquid specimen may be effectively collected as much as possible with a minimized wound, which may help to implement safe and minimally invasive collection of specimens.

In addition, in this embodiment, the length of the piercing portion 32 of the piercing component 30 is not particularly limited, for example, for a liquid specimen in ophthalmology such as aqueous humor, a length that may enable piercing the anterior chamber of the eye and penetration into the interior of the anterior chamber is enough.

In this embodiment, the collection device 1 may further have a sleeve cap 40 (see FIG. 3). In some examples, the sleeve cap 40 is detachably mounted to the piercing component 30. As shown in FIG. 3 and FIG. 9, by assembling the reservoir 10, the delivery tube 20, the piercing component 30, and the sleeve cap 40 together, it may be ensured that the collection device 1 is under protection, and the piercing component 40 is prevented from injuring an operator such as a doctor by improper operation. Furthermore, the sleeve cap 40 may also block dust and prevent the piercing component 30 from being contaminated by dust or other pollutants.

In some examples, the sleeve cap 40 may be an airtight cap covering the piercing component 30. Therefore, the negative pressure state of the reservoir 10 may be further ensured.

In addition, in some examples, the sleeve cap 40 may cover both the piercing component 30 and the valve 23. In such case, the valve 23 may also be protected by the sleeve cap 40 so that the valve 23 may prevented from a misoperation. Here, the tail end of the sleeve cap 40 may be subjected to adaptive adjustment according to the structure of the valve 23 to matingly cover the valve 23.

In some examples, the sleeve cap 40 may be made of materials such as plastics, glass, or metal. In some examples, the sleeve cap 40 may be in a variety of shapes such as a cylinder, a cuboid, a polygonal prism, or an irregular shape.

In some examples, the sleeve cap 40 may be provided with non-slip ribs on an outer wall (see FIG. 9). In some examples, numerous non-slip ribs 41 may be provided, for example, four, eight or twelve non-slip ribs are provided in a peripheral direction of the sleeve cap 40. In some examples, the non-slip ribs 41 may be provided in a length direction of the sleeve cap 40 and formed to have an elongated shape.

In addition, in some other examples, the sleeve cap 40 may be further provided with projections on the outer wall. In some other examples, the sleeve cap 40 may be further provided with a non-slip sleeve on the outer wall. Therefore, slipping during use may be prevented.

While the invention has been particularly described with reference to the drawings and embodiments, it will be understood that the foregoing description is not intended to limit the invention in any way. This invention may be modified and changed by those skilled in the art without deviating from the spirit and scope of the disclosure, and such modifications and changes all fall within the protection scope of the claims of the disclosure.

Figure 11:
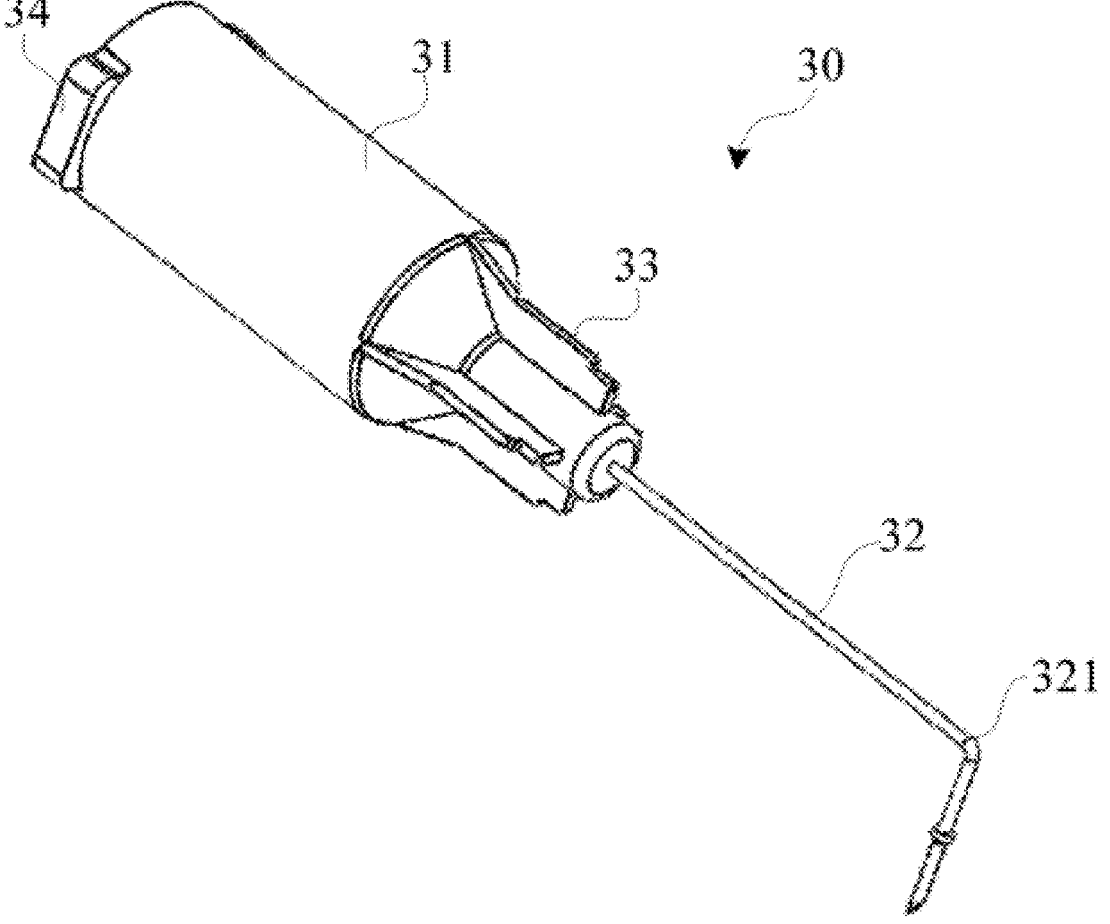
FIG. 11 is a schematic diagram of the collection device according to an embodiment of the disclosure.

For example, in the collection device 1, the angle θ formed by the extension line of the delivery inlet 21 and the extension line of the delivery outlet 22 is 180 degrees, that is, the delivery tube 20 is formed to have an elongated shape. At the same time, the piercing component 30, particularly the piercing portion 32 of the piercing component 30, may be configured to have a bent shape, as shown in FIG. 11. In such case, the piercing portion 32 of the piercing component 30 may have a bent portion 321. Therefore, the operator may push the delivery tube 20 from different angles, and such a structure is particularly suitable for the collection of a liquid specimen in the eye such as aqueous humor.

In some examples, the bent portion 321 may have a bent angle of, for example, 30 degrees, 45 degrees, 60 degrees, 90 degrees, et cetera. In some examples, the bent portion 321 may be made of a memory metal material. Therefore, the bent angle may be adjusted depending on the case to adapt to collection at different sites Various embodiments of the disclosure may have one or more of the following effects.

In some embodiments, the disclosure provides a collection device with a valve for a liquid specimen, which is not only simple and convenient to operate, but also safe and reliable.

In other embodiments, the disclosure provides a collection device with a valve for a liquid specimen including a reservoir, a delivery tube, and a piercing component. A doctor or other professionals may collect a liquid specimen conveniently and safely via an automatic process by piercing a tissue (such as the anterior chamber of the eye) with the piercing component and may conveniently perform subsequent tests directly on the collected liquid specimen stored in the reservoir.

In further embodiments, an operator such as a doctor, a nurse, or any other professional person may conveniently collect a liquid specimen via an automatic process under negative pressure by piercing a tissue (such as in the anterior chamber or in the vitreous body of the eye) with the piercing component. They may also conveniently perform subsequent tests directly on the collected liquid specimen stored in the reservoir so that the collection device is particularly functional for collecting aqueous humor and vitreous humor in ophthalmology.

In an clinical surgery of ophthalmology, the collection of a liquid specimen is generally difficult, for example, the amount of collected aqueous humor is generally no more than 100 μL, therefore, how to guarantee the amount of a liquid specimen to be collected and prevent excessive collection is always difficult for clinical practice in ophthalmology. In some embodiments of the disclosure, by adopting a negative pressure collection device having a controlling valve, the difficulties may be effectively overcome, and it may help to ensure that a doctor or other professionals may collect a liquid specimen such as aqueous humor in a required amount safely and reliably.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A collection device with a valve for a liquid specimen, comprising:

a reservoir having a sealed cavity for storing the liquid specimen, wherein:

the sealed cavity has a fixed volume; and the sealed cavity is sealed by an airtight plug, wherein the airtight plug is configured to accommodate a depressurization means such that the fixed volume of the sealed cavity can be depressurized to a vacuum and maintain a set negative pressure;

a delivery tube in communication with the sealed cavity of the reservoir and having a delivery inlet, a delivery outlet, and the valve, wherein:

the valve is disposed between the delivery inlet and the delivery outlet, the valve is configured to control communication and blocking between the delivery inlet and the delivery outlet, and an angle is formed by an extension line of the delivery inlet and an extension line of the delivery outlet; and a piercing component for piercing a tissue and in communication with the delivery inlet of the delivery tube, wherein:

the valve includes a pressing unit, a rod body connected to the pressing unit, an inner cavity cooperating with the rod body, a first seal ring and a second seal ring separately arranged at different positions on the rod body, and an elastic component provided in the inner cavity;

the delivery inlet, the delivery outlet, and the piercing component are in communication when the rod body is at a first position;

the delivery inlet is not in communication with the delivery outlet when the rod body is at a second position;

the airtight plug is provided at one end close to the delivery outlet of the delivery tube; and the airtight plug is radially positioned at a cone shaped portion of the delivery tube such that a part of a top surface of the airtight plug is above a cone surface and another part of the top surface of the airtight plug is below the cone surface.

2. The collection device according to claim 1, wherein the reservoir is detachably connected to the delivery tube.

3. The collection device according to claim 1, wherein the valve is a press-type mechanical valve.

4. The collection device according to claim 3, wherein when the pressing unit is pressed, the delivery inlet is in communication with the delivery outlet.

5. The collection device according to claim 1, wherein the liquid specimen is aqueous humor in an eye.

6. The collection device according to claim 5, wherein the piercing component is provided with a limit mechanism for limiting a piercing position.

7. The collection device according to claim 5, wherein the sealed cavity has a volume of 0.05 mL to 0.50 mL.

8. The collection device according to claim 1, wherein the angle formed by the extension line of the delivery inlet and the extension line of the delivery outlet is 30-120 degrees or 180-300 degrees.

9. The collection device according to claim 1, wherein the reservoir is a transparent tube.

10. The collection device according to claim 9, wherein the reservoir is provided with scales.

11. The collection device according to claim 1, further comprising a sleeve cap detachably covering the piercing component.

12. The collection device according to claim 11, wherein the sleeve cap is further provided with non-slip ribs.

13. The collection device according to claim 1, wherein the piercing component is a syringe.

14. The collection device according to claim 1, wherein the sealed cavity is under the negative pressure relative to an intraocular pressure.

15. The collection device according to claim 1, wherein the connection between the reservoir and the delivery tube is a Luer connection.

16. The collection device according to claim 1, wherein the connection between the piercing component and the delivery tube is a Luer connection.

17. The collection device according to claim 1, wherein the piercing component is integrally formed with the delivery tube.

18. The collection device according to claim 1, wherein a narrow channel is formed inside the reservoir, the delivery tube, and the piercing component.

19. A collection device with a valve for a liquid specimen, comprising:

a reservoir having a sealed cavity for storing the liquid specimen, wherein:

the sealed cavity has a fixed volume; and the sealed cavity is sealed by an airtight plug, wherein the airtight plug is configured to accommodate a depressurization means such that the fixed volume of the sealed cavity can be depressurized to a vacuum and maintain a set negative pressure;

a delivery tube in communication with the sealed cavity of the reservoir and having a delivery inlet, a delivery outlet, and the valve, wherein:

the valve is disposed between the delivery inlet and the delivery outlet, and the valve is configured to control communication and blocking between the delivery inlet and the delivery outlet; and a piercing component for piercing a tissue and in communication with the delivery inlet of the delivery tube, wherein:

the piercing component comprises a main body and a piercing portion connected to the main body, and the piercing portion has a bent shape,

14 wherein:

the valve includes a pressing unit, a rod body connected to the pressing unit, an inner cavity cooperating with the rod body, a first seal ring and a second seal ring separately arranged at different positions on the rod body, and an elastic component provided in the inner cavity;

the delivery inlet, the delivery outlet, and the piercing component are in communication when the rod body is at a first position;

the delivery inlet is not in communication with the delivery outlet when the rod body is at a second position;

the airtight plug is provided at one end close to the delivery outlet of the delivery tube; and the airtight plug is radially positioned at a cone shaped portion of the delivery tube such that a part of a top surface of the airtight plug is above a cone surface and another part of the top surface of the airtight plug is below the cone surface.

* * * * *